United States Patent [19]

Mutai et al.

[11] 4,435,389
[45] Mar. 6, 1984

[54] COMPOSITION FOR PROMOTING GROWTH OF BIFIDOBACTERIA

[75] Inventors: Masahiko Mutai, Higashi Yamato; Tsuneo Terashima, Musashi Murayama; Tokutaro Takahashi, Tokyo; Ryuichiro Tanaka, Tachikawa; Akio Kuroda, Nishinomiya; Sadao Ueyama, Kobe; Keisuke Matsumoto, Fujiidera, all of Japan

[73] Assignee: Kabushiki Kaisha Yakult Honsha, Tokyo, Japan

[21] Appl. No.: 166,463

[22] Filed: Jul. 7, 1980

[51] Int. Cl.$^3$ .................. A61K 31/71; C12P 19/04
[52] U.S. Cl. ............................ 424/181; 424/180; 435/244; 536/1.1; 536/123
[58] Field of Search .................. 536/1, 1.1, 123; 424/180

[56] References Cited

U.S. PATENT DOCUMENTS

| | | | |
|---|---|---|---|
| 4,067,748 | 1/1978 | Rowe | 536/1 |
| 4,225,673 | 9/1980 | Sugiura et al. | 536/1 |
| 4,229,440 | 10/1980 | Murofushi et al. | 536/1 |
| 4,238,473 | 12/1980 | Lemieux et al. | 536/1 |

FOREIGN PATENT DOCUMENTS 49-40956 11/1974 Japan.
49-40957 11/1974 Japan.

OTHER PUBLICATIONS

Worbe et al., "Chem. Abst.", vol. 68, 1968, p. 37, 423v.
Lee et al., "Chem. Abst.", vol. 89, 1978, p. 48, 947(d).

Primary Examiner—Johnnie R. Brown
Attorney, Agent, or Firm—Wenderoth, Lind & Ponack

[57] ABSTRACT

This invention relates to a composition for promoting growth of Bifidobacteria containing as effective constituent an oligosaccharide represented by the general formula Gal-(gal)$_n$-Glc, wherein Gal denotes a galactose residue, Glc a glucose residue and n an integer of 1 to 4.

This invention further relates to a method for manufacture of the material for promoting growth of Bifidobacteria characterized in that lactose or a lactose-containing material is treated with β-galactosidase produced by *Aspergillus oryzae*.

1 Claim, 6 Drawing Figures

COMPOSITION FOR PROMOTING GROWTH OF BIFIDOBACTERIA

BACKGROUND OF THE INVENTION

This invention relates to a composition capable of promoting growth of bifidobacteria, and the method for manufacture thereof.

A number of substances capable of promoting growth of bifidobacteria (hereinafter referred to as Bifidus growth factors) have been reported, and proposals have been made of a variety of manufacture methods thereof and powdered milk containing such substances, as described in the Japanese Patent Publications Nos. 32908/66, 6510/70, 6865/70, 21606/70, 40956/74 and 40957/74. However, most of the Bifidus growth factors reported so far have been found to be effective only through culture tests conducted outside of the living body, the activity of these factors outside of the living body remaining thus unclear or largely unsatisfactory.

Bifidobacteria is a useful bacterium living in human intestines with its well-known physiological significance. Needless to say, efforts have been made to elevate the ratio which said bacterium occupies among a number of bacteria living in intestines of artificially fed infants. Aside from the case of using the Bifidus growth factors only for growth of bifidobacteria outside of a living body, Bifidus growth factors to be contained wilfully in food or culture media should desirably exhibit positive and sufficient effects within the living body as well, and thus demand has been made for Bifidus growth factors which are superior from this aspect.

SUMMARY OF THE INVENTION

The object of the present invention is to provide Bifidus growth factors that may exhibit high activity in the living body and thus satisfy the above demand.

This object may be attained by the present invention by a composition for promoting growth of bifidobacteria containing as effective constituent an oligosaccharide having the general formula Gal-(Gal)$_n$-Glc, wherein Gal denotes a galactose residue, Glc a glucose residue and n an integer of 1 to 4.

The present invention also resides in a method for manufacture of a material for promoting growth of bifidobacteria characterized in that lactose or a lactose-containing material is treated with $\beta$-galactosidase produced by *Aspergillus oryzae*.

DESCRIPTION OF THE PREFERRED EMBODIMENT

Most of the above oligosaccharides, which are the effective constituents contained in the inventive Bifidobacteria growth promoting composition or Bifidus growth factor, have been discovered by the present inventors during their research into transfer reactions taking place along with a hydrolysis reaction when lactose is acted upon by $\beta$-galatosidase. Many reports have been made of the above transfer reaction since the first one made by Wallenfels in 1951. The transferred oligosaccharides, on which reports have been made of their possibility of isolation, are disaccharides, namely Gal-($\beta$-1,2)-Glc, Gal-($\beta$-1,3)-Glc, Gal-($\beta$-1,6)-Glc, Gal-($\beta$-1,3)-Gal and Gal-($\beta$-1,6)-Gal and trisaccharides, namely, Gal-($\beta$-1,6)-Gal-($\beta$-1,4)-Glc and Gal-($\beta$-1,6)-Gal-($\beta$-1,6)-Glc, wherein the mode of galactoside linkage is indicated within brackets. The presence of tetrasaccharides has been confirmed by Huber et al, but the structure thereof has not been clarified. Production of polysaccharides including pentasaccharides has not been reported. The contents of these reports are limited to the clarification of the transfer mechanism and studies of the structure of oligosaccharides thus produced, and no reports has been made of the relation between the transferred oligosaccharides and the growth of Bifidobacteria.

The oligosaccharide, which is the Bifidus growth factor and has the above general formula (hereinafter, this specific oligosaccharide is meant by the term "oligosaccharide") may be produced by treating lactose with $\beta$-galactosidase produced by *Aspergillus oryzae*. Following this treatment, there exist in the reaction mixture non-reacted lactose as well as galactose and glucose produced by hydrolysis. Therefore, in order to obtain a product having higher activity as Bifidus growth factors, the oligosaccharide concentration need be elevated by carrying out a suitable refining step following enzyme treatment, by selecting enzyme treatment conditions that will give a higher oligosaccharide ratio, or by combination thereof.

The method of the present invention for manufacture of a material for promoting growth of Bifidobacteria will be explained below in more detail.

Commercially available lactose may be used as it is for treatment by $\beta$-galactosidase, it being unnecessary to use specially refined one. Whole milk or skim milk containing lactose as constituent may also be used as starting material.

For enzyme treatment, substrate concentration of 10 to 50%; pH of 3 to 8; enzyme concentration of 1 to 100 units; and the temperature of 20° to 50° C. may be preferred.

Figure 1:
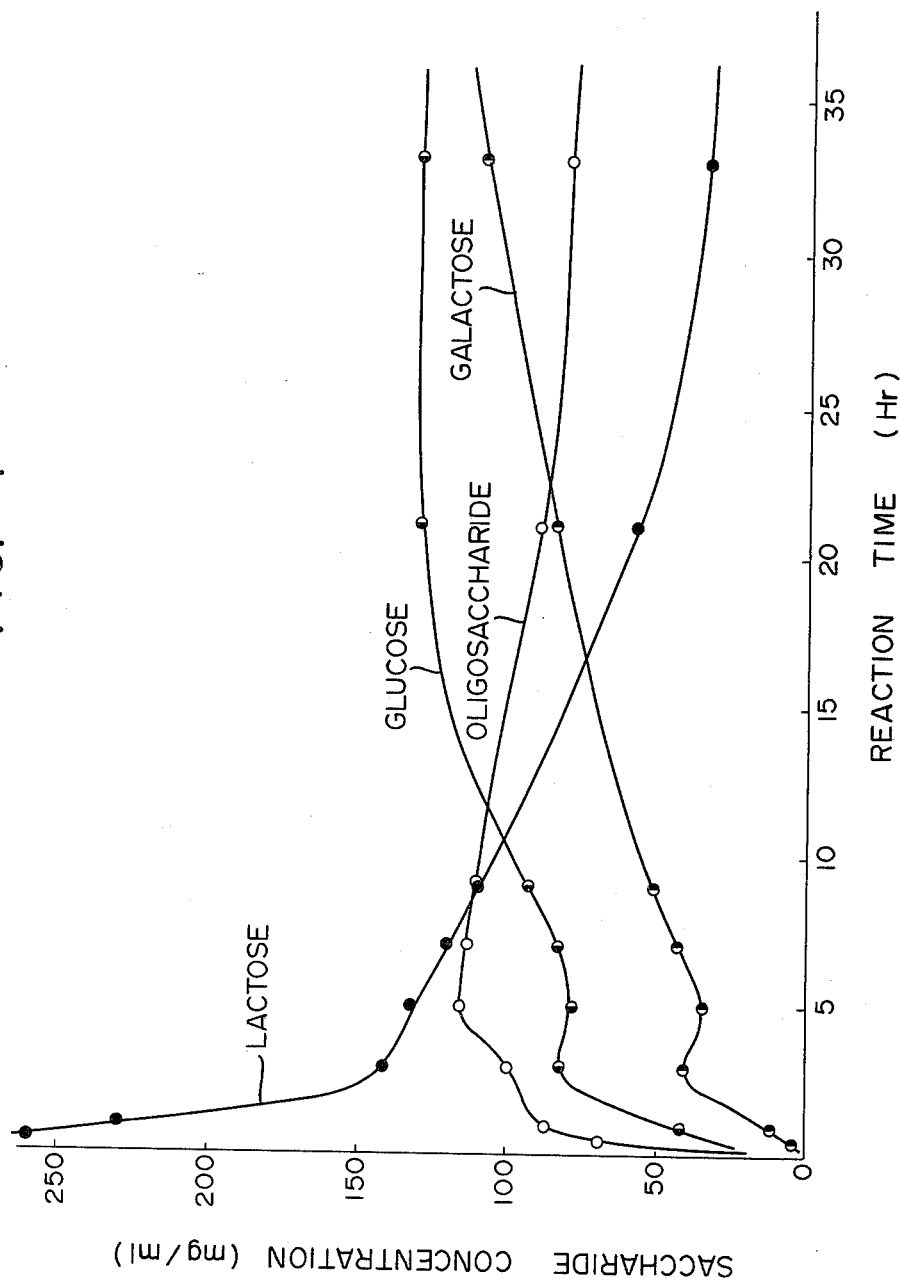
FIG. 1 is a graph showing the relation between the saccharide yield and reaction time in the case of treating lactose with $\beta$-galactosidase.

The reaction time has a marked effect on oligosaccharide yield. As seen from FIG. 1 showing the relation between the reaction time and the amount of the resulting saccharide in a typical enzyme treatment, glucose, galactose and oligosaccharide increase in quantity substantially linearly at the initial stage of reaction but follow thereafter rather complicated curves, whereas the oligosaccharide will be reduced in quantity as from a certain time point. The time at which the oligosaccharide yield will be maximum may depend on other factors as well and hence the optimum reaction time should preferably be decided through experiments.

The oligosaccharide contained in the reaction mixture may be separated from other constituents by thin layer chromatography and determined by the Anthrone method.

The enzyme reaction may be terminated by heating the reaction mixture for 5 to 10 min. at higher than 90° C.

The reaction mixture following an enzyme treatment may be used as Bifidus growth factors or a composition such as dairy products containing same, either as it is or after suitable concentrations or drying to a powdered form. The reaction mixture may be subjected to purification as the occasion may demand for elevating the concentration of the effective constituent, namely, oligosaccharide. The purification may be carried out in a number of ways such as by preliminary refining of the reaction mixture with an ion exchange resin followed by passage through an activated charcoal column for adsorbing oligosaccharide thereto, and eluation with aqueous alcoholic solutions. It is also possible to inoculate mono- and disaccharide fermentable micro-organisms to the reaction mixture for culture and consumption of mono- and disaccharides for more facilitated isolation of oligosaccharides.

In the below there is illustrated an analytic example of oligosaccharide contained in the inventive composition, namely that according to the Example 1 which is described below and carried out under standard conditions.

(a) molecular weight distribution

Figure 2:
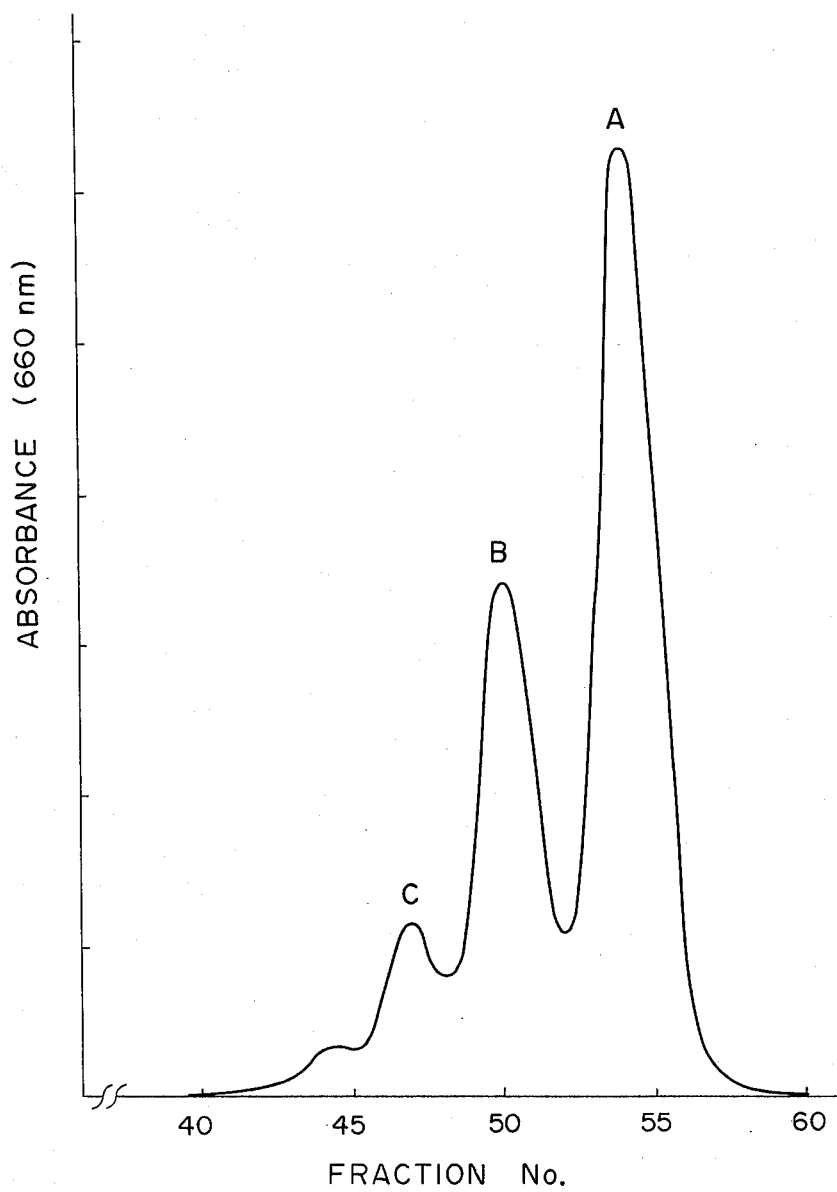
FIG. 2 is a graph showing the result of experiment of gel filtration by oligosaccharides.

FIG. 2 shows the result of gel filtration with Bio-Gel P-2. Peaks A, B and C correspond to tri-, tetra- and pentasaccharides, respectively, with the composition ratio as calculated from the area ratio of these peaks being about 55% for trisaccharide, about 32% for tetrasaccharide and about 13% for pentasaccharide and higher saccharides.

(b) constituent saccharide

Lactose, oligosaccharide (not separated into its constituents) and tri- and tetrasaccharides of the oligosaccharide were hydrolyzed at 100° C. for 4 hours in a 0.5 N-HCL solution. The same product was also hydrolyzed at 50° C. for 4 hours with $\beta$-galactosidase. The molar ratios of the resulting saccharides for these respective cases are illustrated in the following Table 1. It is seen from this Table that the molar ratios glucose/galactose for tri-, tetra- and pentasaccharides of the oligosaccharide amount to 1:2, 1:3 and 1:4, respectively.

TABLE 1

| | galactose/glucose | |
|---|---|---|
| | acidic hydrolysis | enzyme decomposition |
| lactose | 0.98 | 0.98 |
| oligosaccharide | 2.44 | 2.42 |
| trisaccharide | 1.94 | 1.92 |
| tetrasaccharide | 2.88 | 2.84 |
| pentasaccharide | 3.82 | 3.80 |

(c) mode of linkage of constituent saccharides

From a product obtained by partial acid hydrolysis of main constituents of trisaccharide (as separated at the active charcoal column chromatography), the presence of lactose and Gal-($\beta$-1,6)-Gal was confirmed, in addition to glucose and galactose. From this result, and the glucose/galactose ratio in the wholly hydrolyzed product being 1:2, the trisaccharide structure was estimated to be Gal-($\beta$-1,6)-Gal-($\beta$-1,4)-Glc.

As a result of our similar analyses of a number of oligosaccharide constituents, it has been discovered that the oligosaccharide has the above general formula and that galactose-galactose linkage is $\beta$-1,3, $\beta$-1,4 or $\beta$-1,6 linkage, with the $\beta$-1,6 linkage being predominant and the galactose-glucose linkage is $\beta$-1,3, $\beta$-1,4 or $\beta$-1,6 linkage with the $\beta$-1,4 linkage being predominant.

As discussed above, so far as isolated oligosaccharides of the inventive composition, are concerned, it may be affirmed that the individual oligosaccharides per se act as Bifidus growth factors, not to speak of a mixture of various oligosaccharides which will operate excellently for promoting the growth of bifidobacteria.

The special advantage of the oligosaccharide contained in the inventive composition is that the operation thereof is highly effective not only outside but also inside of the living body.

The growth promoting operation for Bifidobacterium proper to the inventive composition has substantially no relation with the species of bifidobacteria and thus may be effective with *Bifidobacterium breve, Bifidobacterium bifidum, Bifidobacterium infantis, Bifidobacterium adolescentis* etc. living fixedly in human intestines.

The inventive composition may be reaction products obtained by treating highly purified oligosaccharide itself or any mixture containing oligosaccharide such as lactose or a lactose-containing material with $\beta$-galactosidase to oligosaccharide; powdered or fermented milk or the like food or medicine consisting of a secondary product of such reaction product or any desired food or medicine added with purified oligosaccharides.

The present invention will be further described by referring to several examples in which Bidfidobacterium has been identified as "B".

EXAMPLE 1

3.6 kg of lactose was dissolved in about 6 liters of warm water to which were added 50 ml of 1 M-acetic acid buffer solution ($p^H$, 4.6), 100,000 units of $\beta$-galactosidase and water to a 10 liter solution which was then reacted at 37° C. for 5 hours. The reaction solution was then heated for denaturing enzyme, the denatured protein was filtered off and the remaining solution was passed through a column of anionic exchange resin and a column of cationic ion exchange resin. The filtrate was contacted overnight with a 30×30 cm column filled with active charcoal. The active charcoal was washed with 60 liters of deionated water for eluation of monosaccharides. The active charcoal thus treated was then eluated with 60 liters of 5% ethanol and 60 liters of 50% ethanol in this order. The eluate obtained with the 50% ethanol was concentrated to about 7 liters, filtered in germ-free manner through a membrane filter (pore size, 0.2$\mu$) and again subjected to ion exchange to a transparent saccharide solution. The solution was concentrated in vacuum to a viscous solution of about 2.5 liters which again was filtered through a membrane filter and the filtrate solution was freeze dried to white oligosaccharide powders (hereafter stated as TOS).

EXAMPLE 2

Figure 3:
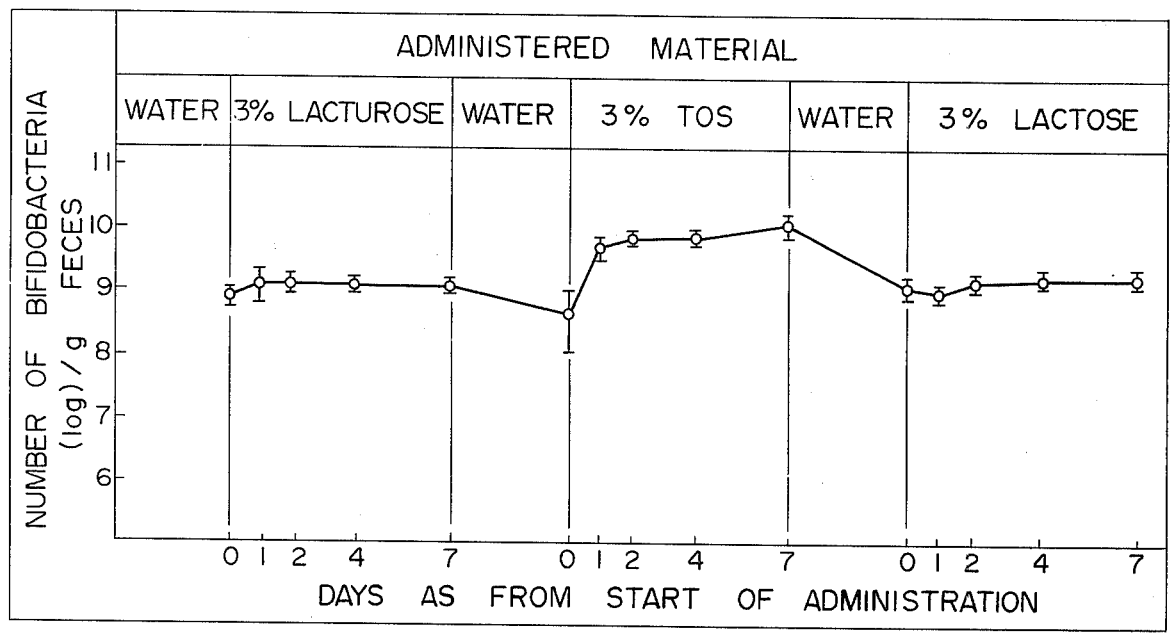
FIG. 3 is a graph showing the result of experiment of the Example 2.

To 6 adult germ-free Fischer series female rats were administered 10 different bacteria (including B. breve) separated from human feces and these bacteria were made to be fixed in the intestines. Then, (a) a 3% aqueous solution of lacturse, (b) a 3% aqueous solution of TOS obtained from the Example 1 and (c) a 3% solution of lactose were administered daily for 1 week periods in the order of (a) to (c). The solutions were administered in amounts of 0.6 g per day as solid material, and 1 week rest periods were provided for changeover between the different solutions. During the interval, the rat feces were taken for measuring the number of live *B. breve* bacteria contained in the feces. The result is shown in FIG. 3.

As seen from this Figure, the number of *B. breve* bacteria is increased by about 10 times by administration of TOS. Only minor increase in the number of the bacteria may be noted by administration of lactose, whereas no change is used for the case of lacturose administration.

EXAMPLE 3

The following experiment was conducted with 6 adult common Fischer series male rats. The bifidobacteria used was *B. breve* or *B. infantis* which were obtained in such manner that bacteria resulting from 48 hour culture on VL-G medium and ensuing centrifugal separation were made to float in a milk culture medium and administered as it was. The administered amount was $2 \times 10^8$ per day in terms of the number of bacteria and 20 ml per day of 5% aqueous solution of TOS.

(a) The rats were made to drink only the bacterial solution only one day.
(b) The rats were administered every day for the second week only with bacterial solution.
(c) The bacterial solution and TOS were administered every day for the third week.
(d) Only TOS was administered every day for the fourth week.

Figure 4:
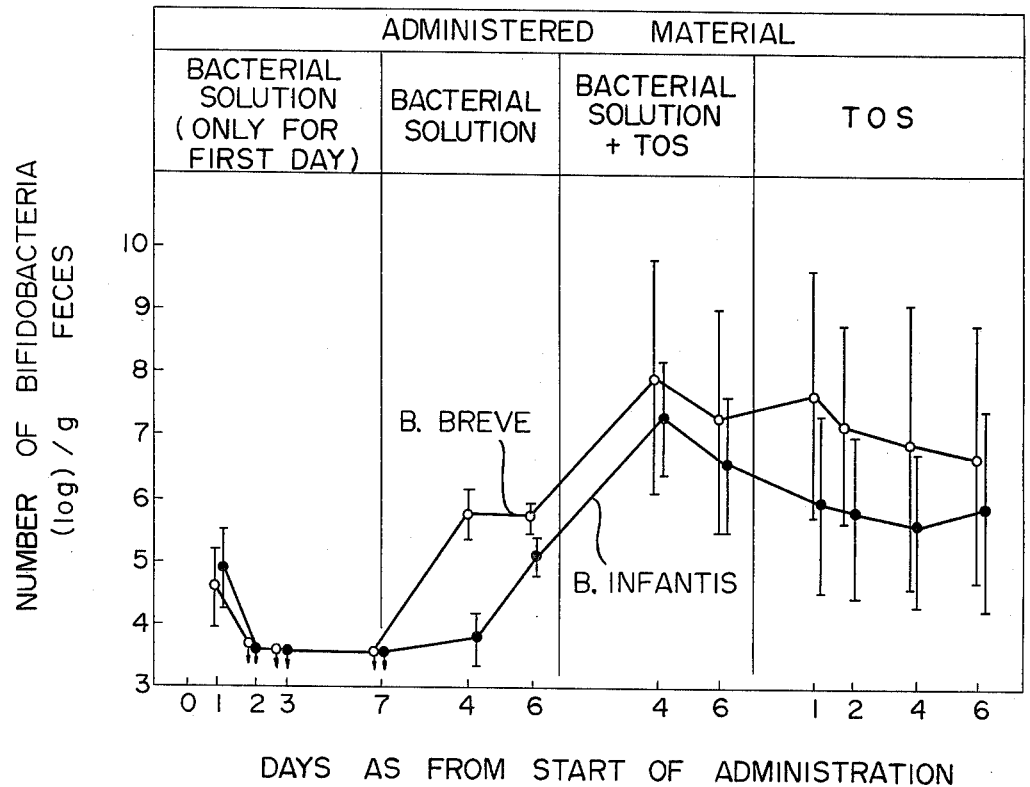
FIG. 4 is a graph showing the result of experiment of the Example 3.

FIG. 4 shows the result of the measured number of live bacteria of B bacteria (of the kinds as administered) contained in the rat's feces.

It may be seen from this Figure that the number of B bacteria in intestines is increased markedly by parallel administration of the bacterial solution and TOS and that the number of bacteria may be maintained upon interruption of the administration of the bacterial solution.

EXAMPLE 4

The following experiment was conducted with 5 healthy adult men. The bacterial solutions as administered was that of *B. breve* obtained in the same way as in the Example 3.

Experiment schedule
first week: administration only of bacterial solution
second week: administration of bacterial solution and TOS (3 g per day)
third week: administration of bacterial solution and TOS (10 g per day)
Number of administered bacteria: $10^9$ per day
The way of administering TOS: Dissolved in lukewarm water to be drunk after lunch
Measurement: On the third, fifth and seventh days of the respective weeks, the numbers of the *B. breve* bacteria in the excrements of each man under test were measured and averaged for the respective weeks.

Figure 5:
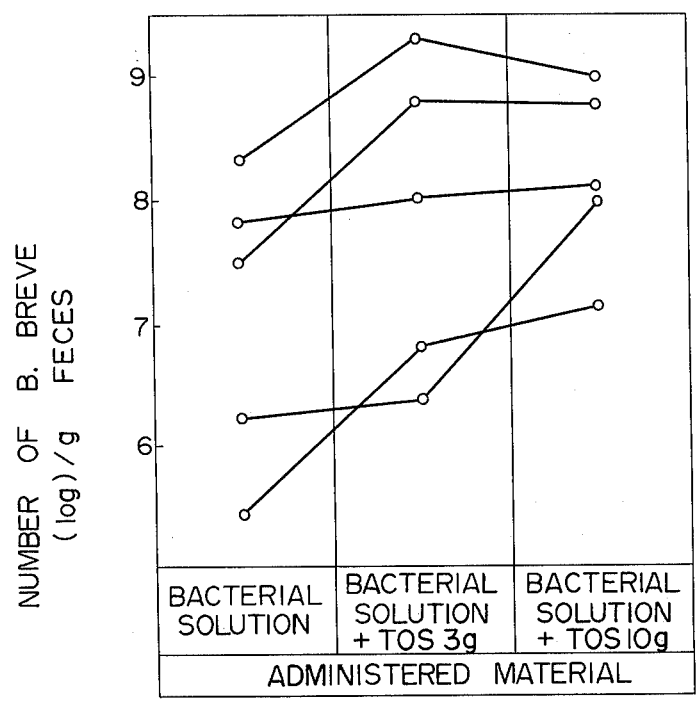
FIG. 5 is a graph showing the result of experiment of the Example 4.

The result of the experiments are as shown in FIG. 5, from which it is seen that the number of the B bacteria is increased markedly by TOS administration.

EXAMPLE 5

The following experiment was conducted with 5 healthy adult men.

| Experiment schedule | No TOS administration |
|---|---|
| first week | No TOS administration |
| second week | 3 g per day of TOS |
| third week | 10 g per day of TOS |

The way of administering TOS: same as in Example 4
Measurement: The total number of bifidobacteria in excrements were measured in the same way as in Example 4.

Figure 6:
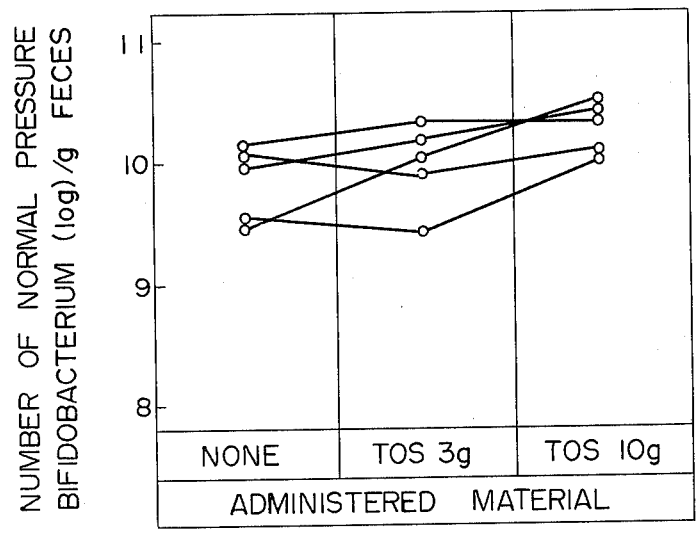
FIG. 6 is a graph showing the result of experiment of the Example 5.

The result of the experiment is shown in FIG. 6 from which it is seen that the number of bifidobateria fixedly living in human intestines may be increased by TOS administration.

EXAMPLE 6

To 1000 liters of reduced skim milk were added ten million units of β-galactosidase of *Aspergillus Oryzae*. The resulting product was maintained at 40° C. for 2 hours and heated for inactivation of enzyme and sterilization. The resulting product was transferred to a culture tank, innoculated with starter of bifidobacteria, cultured at 37° C. for 24 hours, added with sweeteners etc. and homogenized to a fermented milk containing both oligosaccharide and bifidobacteria.

What we claim is:

1. A composition for promoting growth of bifidobacteria consisting essentially of a mixture of oligosaccharides represented by the general formula Gal-(Gal)$_n$-Glc, wherein Gal denotes a galactose residue, Glc a glucose residue and n an integer of 1 to 4, and in which the galactose-galactose linkage is β-1,3, β-1,4 or β-1,6 with the β-1,6 linkage being predominant and the galactose-glucose linkage is β-1,3, β-1,4 or β-1,6 with the β-1,4 linkage being predominant; said oligosaccharides being produced by reacting lactose or a lactose-containing material with β-galactosidase produced by *Aspergillus oryzae* at a temperature and time sufficient to produce said composition.

* * * * *